United States Patent [19]

Knutson

[11] Patent Number: 5,545,672
[45] Date of Patent: Aug. 13, 1996

[54] TREATMENT OF INSULIN RESISTANCE AND TYPE 2 DIABETES MELLITUS WITH A THIOL PROTEASE INHIBITOR

[75] Inventor: Victoria P. Knutson, Houston, Tex.

[73] Assignee: The University of Texas System, Houston, Tex.

[21] Appl. No.: 272,292

[22] Filed: Jul. 8, 1994

Related U.S. Application Data

[63] Continuation of Ser. No. 16,689, Feb. 11, 1993, abandoned.

[51] Int. Cl.$^6$ .............. A61K 31/18; A61K 38/00; A61K 38/55
[52] U.S. Cl. .............. 514/603; 514/18; 514/71; 514/475; 514/866
[58] Field of Search .............. 514/475, 18, 71, 514/866, 603

[56] References Cited

U.S. PATENT DOCUMENTS

| | | | |
|---|---|---|---|
| 3,810,931 | 5/1974 | Guthrie | 260/956 R |
| 4,132,719 | 1/1979 | Mohrbacher | 260/348.61 |
| 4,132,720 | 1/1979 | Mohrbacher | 260/348.61 |
| 4,196,300 | 4/1980 | Mohrbacher | 549/90 |
| 4,324,796 | 4/1982 | Eistetter et al. | 424/278 |
| 4,337,267 | 1/1982 | Eistetter et al. | 424/278 |
| 4,418,075 | 11/1983 | Tamai et al. | 424/278 |
| 4,430,339 | 2/1984 | Eistetter et al. | 424/278 |
| 4,499,294 | 5/1985 | Maryanoff | 514/519 |
| 4,732,910 | 3/1988 | Yaginuma et al. | 514/475 |
| 4,764,623 | 8/1988 | Kees | 548/253 |
| 4,788,306 | 11/1988 | Schiehser et al. | 549/549 |
| 4,829,087 | 5/1989 | Ammon | 514/562 |
| 5,055,451 | 8/1990 | Krantz et al. | 514/19 |
| 5,124,314 | 7/1991 | Cooper | 514/4 |

FOREIGN PATENT DOCUMENTS

| | | |
|---|---|---|
| 20025192 | 6/1990 | European Pat. Off. . |
| 55-035012 | 6/1985 | Japan . |
| 55-145678 | 7/1986 | Japan . |
| 2040919 | 8/1991 | United Kingdom . |
| WO82/00643 | 3/1982 | WIPO . |

OTHER PUBLICATIONS

Docherty et al *Proc. Nat. Acad. Sci USA* 79:4613–4617 (1982).
Azuma et al., *Curr Eye Res*, 10:657–666, 1991.
Baricos et al., *Biochem Biophys Res Commun*, 155:1318–1323, 1988.
Barrett, et al., *Biochem J.*, 201:189–198, 1982.
Daston et al., *Teratology*, 43:253–261, 1991.
Grinde, *Biochem Biophys Acta*, 701:328–333, 1982.
Guy-Bruno, *Chemical Abstracts*, No. 11607051530, 1991.
Hanada et al., *Proteinase Inhibitors: Medical and Biological Aspects*, 25–36, 1983.
Hashida, et al., *J. Biochem*, 88:1805–1811, 1980.
Hofmann, et al., *Diabetes Care*, 15:1075–1078, 1981.
Karam, John H., Chapter 40 Pancreatic Hormones & Antidiabetic Drugs, 586–601, 1982.
Knutson, V., *J. of Biological Chemistry*, 266:15656–15662, 1991.
Kobayashi et al., *Endocrinol. Japon*, 36:833–844, 1989.
Kobayashi et al., *Diabetes*, 41:476–483, 1992.
Redwood et al., *Cancer*, 69:1212–1219, 1992.
Taisho, *Pharma Projects*, PJB Publications Ltd., Richmond, Surrey, UK, 1988.
Umezawa, *Methods in Enzymol*, 45:678–695, 1976.
Groop, L. C., *Diabetes Care*, 15:737–754, 1992.
Groop & Pelkonen, *Acta Endocrinol. Supp.*, 262:131–135, 1984.
Knutson & Buck, *Arch. Biochem. Biophys.*, 285:197–204, 1991.
Tarlow, et al., *J. Cell Biol.*, 73:332–353, 1977.

*Primary Examiner*—Theodore J. Criares
*Attorney, Agent, or Firm*—Pravel, Hewitt, Kimball & Krieger

[57] ABSTRACT

Pharmaceutical compositions and methods for treatment of insulin-resistance and diabetes mellitus using thiol protease inhibitors such as E-64.

5 Claims, No Drawings

TREATMENT OF INSULIN RESISTANCE AND TYPE 2 DIABETES MELLITUS WITH A THIOL PROTEASE INHIBITOR

REFERENCE TO GOVERNMENT GRANTS

Some of the work which led to the invention described herein was developed under a funding agreement with the government of the United States of America. The government may have certain rights to this invention.

This is a continuation of application Ser. No. 08/016,689 filed on Feb. 11, 1993 now abandoned.

FIELD OF THE INVENTION

This invention relates to a pharmaceutical composition and method for the treatment of Type 2 diabetes mellitus and insulin resistance. More particularly, a thiol protease inhibitor is administered to a diabetic patient to reduce insulin resistance.

BACKGROUND OF THE INVENTION

Diabetes mellitus is a syndrome characterized by abnormal insulin secretion associated with fasting hyperglycemia and decreased glucose tolerance. A National Diabetes Data Group (NDDG) of the National Institutes of Health distinguishes five subclasses of diabetes. These include insulin-dependent diabetes mellitus (Type I), a ketosis-prone type of diabetes associated with histocompatibility antigens on chromosome 6 and with islet cell antibodies, and non-insulin-dependent diabetes mellitus (Type II), a non-ketosis-prone type of diabetes not secondary to other diseases or conditions. Type II diabetes is characterized by tissue insensitivity or resistance to insulin and impaired pancreatic B cell response to glucose. (Karam, J. H., in *Basic Clinical Pharmacology*, 5th Ed., B. G. Katzung, ed, Appleton & Lange, Norwalk, Conn., 1992, pp. 586–601).

The accepted treatment of diabetes mellitus is generally insulin replacement by insulin injection, insulin pump, and the like. The objectives of the treatment are to avoid ketoacidosis and to control symptoms resulting from hyperglycemia and glucosuria.

Chronic treatment with insulin, especially in Type II diabetes mellitus, or the endogenous production of high levels of insulin in many cases results in the development of insulin resistance. Current therapy for treatment of insulin resistance is injection of high doses of insulin to provide greater availability to insulin receptors in the tissues. Very high doses of insulin may ultimately be required, and the resulting high circulating levels of insulin cause some of the side effects associated with insulin resistance such as diabetic nephropathy. This "therapy" may in fact worsen the disease.

Sulfonylurea drugs may be administered as hypoglycemic agents (Katzung B. G., in *Basic and Clinical Pharmacology*, 5th Ed., 1992, p. 585–597), however, these sulfonylurea drugs are effective in overcoming insulin resistance only in a small population of patients (approximately 30%) (Groop, L. C., *Diabetes Care*, 15:737–754, 1992; Groop and Pelkonen, *Acta Endocrinol.* Suppl. 262:131–135, 1984).

Biguanide drugs, while not used in this country, are being tested in clinical trials as hypoglycemic agents (Katzung p. 598–599). Likewise, pioglitazone is being tested in clinical trials as a hypoglycemic agent (Hoffman and Colca, *Diabetes Care*, 15:1075–1078, 1992; Koybayashi et al., *Diabetes*, 41:476–483, 1992. Although these agents are being tested to evaluate usefulness in decreasing insulin resistance, no mechanism has been described to explain how they exert their effects. As has been found with sulfonylureas, the bignanides and pioglitazone may be found to be ineffective in a large percentage of patients, or the effectiveness of the agents may decline with longterm use. New therapeautic agents to decrease insulin resistance need to be identified and brought to clinical practice. To date in the U.S.A., no therapeutic agent is available for clinical use to reduce or eliminate insulin resistance.

The inventors have recently discovered that chronic treatment of cultured cells with high concentrations of insulin, conditions which mimic the hyperinsulinemic state of Type II diabetes mellitus, resulted in the generation of a cytosolic fragment of the insulin receptor, termed $\beta'$. These studies also showed that the irreversible thiol protease inhibitor, E-64, inhibited the production of the insulin receptor fragment $\beta'$. (V. P. Knutson, *The Journal of Biological Chemistry*, 266:15656–15652, Aug. 25, 1991.) Co-incubation of partially purified, intact insulin receptor with increasing concentrations of the $\beta'$ fragment led to the dose-dependent inhibition of insulin-induced receptor autophosphorylation, the first step in the insulin signal transduction cascade. Without wishing to be bound by theory, it is hypothesized that the $\beta'$ fragment, by inhibiting insulin signal transduction, may mediate insulin resistance. It would therefore be highly desirable to provide a pharmaceutically acceptable agent which would effectively reduce the levels of the insulin receptor $\beta'$ fragment in diabetic patients, and thereby reduce or eliminate insulin resistance.

SUMMARY OF THE INVENTION

The present invention provides a therapeutically effective agent which inhibits the production of insulin receptor $\beta'$ fragment and also reduces insulin resistance. Thiol protease inhibitors, for example E-64, significantly inhibit production of the insulin receptor $\beta'$ fragment and significantly reduce insulin resistance associated with hyperinsulinemia.

DETAILED DESCRIPTION OF THE INVENTION

Chronic treatment of cultured cells with high concentration of insulin mimics the hyperinsulinemic state of Type II diabetes mellitus. Such incubations have been shown to result in the generation of a cytosolic fragment of the insulin receptor, $\beta'$. Co-incubation of partially purified, intact insulin receptor with increasing concentrations of the insulin receptor $\beta'$ fragment led to the dose dependent inhibition of insulin induced receptor autophosphorylation, the first step in the insulin signal transduction cascade. The irreversible thiol protease inhibitor, E-64, was shown to inhibit the production of insulin receptor $\beta'$ fragment in cultured cells (Knutson, J. Biol. Chem. 266, 15656–15652, 1991). It has now been found that co-incubation of fat cells with insulin and a thiol protease inhibitor, for example E-64, inhibits the generation of insulin resistance exhibited by these cells when incubated with insulin alone.

In the present invention, a thiol protease inhibitor such as E-64 is administered to a diabetic patient exhibiting symptoms of insulin-resistance, i.e., a patient suffering from Type II diabetes mellitus. The thiol protease inhibitor may be a reversible protease e.g., leupeptin, but preferably is an irreversible thiol protease such as E-64 (L-transepoxysuccinyl-leucylamido (4-guanidino) butane).

Useful thiol protease inhibitors may be selected by incubation studies with insulin-responsive cultured cells. Cells are incubated with high concentrations of insulin and the desired thiol protease inhibitor, as described in V. Knutson, JBC 266:15656, 1991, and as described for Example 2. Preferred thiol protease inhibitors will inhibit the production of the β' fragment as compared with control cultures and will reinstate known insulin-dependent effects such as increased lipogenesis in adipocytes. Alternatively, insulin-resistant model animals such as Zucker fatty rats may be used to test the effectiveness of a thiol protease in the method invention, as described in Example 4. In general, an active thiol protease will prevent the increase in serum triglycerides caused by insulin-resistance, as described in Example 4, or, in the appropriate animal model, will decrease serum glucose, and insulin levels. Whole body weight will also decrease.

An example of a particularly useful thiol protease inhibitor is E-64, commercially available from CalBiochem (San Diego, Calif.), Sigma Chemical Co. (St. Louis, Mo.), and Boehringer Mannheim (Indianapolis, Ind.). Other acceptable thiol protease inhibitors include analogs of E-64 (see Hashida et al., *J. Biochem*, 88:1805–1811, 1980; Barrett et al., *Biochem J.*, 201:189–198, 1982; Hanada et al. in: *Proteinase Inhibitors: Medical and biological aspects*, Katunuma et al., editors, Springer Verlaag, Berlin, pp. 25–36, 1983) and the reversible protease inhibitor, leupeptin (see H. Umezawa, *Methods in Enzymology*, 45:678–695, 1976).

The thiol protease inhibitor is administered, by injection alone, or in combination with insulin, or may be administered orally in an appropriate vehicle, e.g., methyl cellulose. A physician may adequately determine the appropriate therapeutic dose of the thiol protease inhibitor to be administered by methods known in the art. The dosage and frequency of administration will vary with mode of administration and with severity of the disease. In general, the dose is sufficient to reduce or eliminate insulin resistance, and preferably is in the range of 0.5 mg/kg to 1000 mg/kg. The maximal dose is limited by potential toxicity of the thiol protease inhibitor, as determined by known toxicity testing methods.

The patient population to be treated by the method of the present invention includes diabetic patients and non-diabetic patients demonstrating insulin-resistance. These include the subpopulation of diabetic patients having Type II diabetes mellitus and those patients observed clinically to demonstrate insulin-resistance. A thiol protease inhibitor is administered, for example, to a patient prior to onset of clinical Type II diabetes mellitus to prevent, delay or reduce the development of overt Type II diabetes mellitus. The pharmaceutical composition of the present invention includes a thiol protease inhibitor, preferably an irreversible inhibitor such as E-64, in a pharmaceutically acceptable vehicle. Pharmaceutically acceptable vehicles include but are not limited to aqueous solutions such as phosphate buffered saline (PBS), or neutralized ammonium bicarbonate. A pharmaceutical formulation may further include a therapeutic dose of insulin. Preparations for oral administration are formulated in a suitable vehicle such as methylcellulose.

EXAMPLES

The invention will be better understood by reference to the following examples.

Example 1

Inhibition of Insulin-Induced Proteolysis of Insulin Receptor β Subunit by E-64

Intact cell monolayers of 3T3-C2 fibroblasts were incubated with leupeptin or E-64 in the presence or absence of insulin for a period of four hours. The amounts of each additive agent were as follows: insulin, 1.7 μM; leupeptin 10 μg/ml; and E-64, 100 μM.

Cell monolayers were scraped into 10 mM triethanolamine, 10 mM acetic acid, 1 mM EDTA, pH 7.4. The cells were disrupted in a Dounce homogenizer and subjected to centrifugation at 265,000×g, 70 min. at 4° C. The pellet was retained as cellular membranes and the supernatant was collected as the cytosolic fraction.

The cellular membranes were detergent-extracted and the extracts were subjected to SDS polyacrylamide gel electrophoresis on a 7.5% gel to resolve the intact β subunit (approximate mass 92 kDa).

Transfer of the cellular proteins from the 7.5% acrylamide gel to nitrocellulose was conducted at 18 V for 18 h, and the intact β subunit and β' fragment were detected as previously described (Knutson and Buck, *Arch. Biochem. Biophys.*, 285:197–204, 1991). Briefly, following transfer, the nitrocellulose was blocked by incubation for 1 h with blot buffer (50 mM Tris, 0.2M NaCl, pH 8) containing 4% non-fat dry milk. Following blocking, the nitrocellulose was incubated with an anti-peptide antibody which specifically recognizes the carboxy-terminal 16 amino acid residues of the insulin receptor β subunit. This domain is contained in both the intact β subunit and the β' fragment. This antibody has been fully characterized and affinity purified (Knutson and Buck, ibid.). The antibody concentration was 5 μg/ml in blot buffer containing 1% non-fat dry milk, and the incubation was allowed to proceed for 2 h at room temperature. The unbound antibody was then removed from the nitrocellulose by 3 washes with blot buffer containing 1% non-fat dry milk and 0.05% Tween-20. The nitrocellulose was then incubated with $^{125}$I-protein A, 0.1 μCi/ml, with the blot buffer containing 1% non-fat dry milk, for 1 h at room temperature. Following a final 5 washes of the nitrocellulose with blot buffer-1% dry milk-0.05% Tween-20, the nitrocellulose was exposed to X-ray film. Autoradiographic intensities were quantitated by densitometric scanning.

Cytosolic β' fragment (approximate mass 61 kDa) was isolated by subjecting the cellular membranes to high speed centrifugation, removing the supernatant, subjecting the supernatant to SDS polyacrylamide gel electrophoresis on a 7.5% gel, transferring the cytosolic proteins to nitrocellulose, and detecting the cytosolic β' fragment by quantitative immunoblot (Western blot) analysis as described above. The β' fragment data was normalized to the maximum level of β' fragment detected after eight hours of insulin treatment. The above-described procedure is as described in Knutson, V. P., *J. Biol. Chem.*, 266:15656–15662 (1991). Results of the quantitative immunoblot analysis are shown in Table 1.

TABLE 1

| TREATMENT | β SUBUNIT % IN MEMBRANES | β' FRAGMENT % IN CYTOSOL |
|---|---|---|
| Control, no additions | 100 ± 13 | 8 ± 5 |
| Insulin | 80 ± 7 | 62 ± 6 |
| E-64 | 143 ± 7 | Trace |

TABLE 1-continued

| TREATMENT | β SUBUNIT % IN MEMBRANES | β' FRAGMENT % IN CYTOSOL |
|---|---|---|
| E-64 + Insulin | 160 ± 15 | Not detectable |
| Leupeptin | 97 ± 7 | Trace |
| Leupeptin + Insulin | 120 ± 17 | Not detectable |

As is demonstrated in Table 1, little or no β' fragment was detected in the cytosol of basal, insulin-free cells. In contrast, within four hours of insulin treatment, the amount of intact β subunit within the cell membranes decreased, and the level of β' fragment in the cytosol was increased. No β' fragment was detected in the cellular membranes, and no intact β subunit was detected in the cell cytosol (data not shown).

As demonstrated in Table 1, when these cells were incubated in the presence of both insulin and the irreversible thiol protease inhibitor E-64, no loss of intact β subunit was demonstrated in the cellular membranes, and, in fact, the amount of intact β subunit in the treated membranes was elevated above control. In addition, the amount of β' fragment in the cytosol was non-detectable. Thus, treatment with E-64 inhibited the generation of the β' fragment seen in the presence of insulin.

Similarly, when cells were incubated with the reversible thiol protease inhibitor leupeptin, qualitatively similar, but less pronounced effects were seen. As shown in Table 1, leupeptin prevented insulin-induced loss of intact β subunit in the cellular membranes, and also prevented generation of the β' cytosolic fragment.

Example 2

Reduction of Insulin Resistance in Adipocytes by E-64

Intact monolayers of 3T3-L1 adipocytes were preincubated in the absence of insulin (control) or for nine hours in the presence of 1.7 μM insulin to induce cellular insulin resistance. Further test incubations included preincubations in the presence of both 1.7 μM insulin and 100 μM E-64, to test the effect of the agent E-64 on insulin resistance. Following preincubation, the treated monolayers were extensively washed to remove any insulin present from the preincubation period. The monolayers were then incubated with insulin, 0, 0.05, or 10 nM for 30 minutes, followed by the addition of 14C-glucose at a final concentration of 25 mM. Incorporation of the radiolabeled glucose proceeded for 30 minutes, after which the cells were washed, lysed, and the cellular lipids extracted into chloroform:methanol (2:1). The amount of radiolabel incorporated into the cellular lipid was then quantified by liquid scintillation counting, and the results are shown in Table 2. This assay procedure is described in Tarlow et al., *J. Cell Biol.*, 73:332–353, 1977.

TABLE 2

| PRE-TREATMENT | INSULIN (nM) | cpm INCORPORATED | FOLD STIMULATION |
|---|---|---|---|
| CONTROL | 0 | 750 | 1 |
|  | 0.05 | 1200 | 1.6 |
|  | 10 | 2300 | 3.1 |
| INSULIN | 0 | 1600 | 1 |
|  | 0.05 | 1900 | 1.2 |
|  | 10 | 1800 | 1.1 |

TABLE 2-continued

| PRE-TREATMENT | INSULIN (nM) | cpm INCORPORATED | FOLD STIMULATION |
|---|---|---|---|
| INSULIN + E-64 | 0 | 600 | 1 |
|  | 0.05 | 1100 | 1.8 |
|  | 10 | 3100 | 5.2 |

As shown in Table 2, the addition of 10 nM insulin to control cells induced a three-fold increase in lipogenesis. When cells were preincubated with insulin, however, no subsequent stimulation of lipogenesis was demonstrated, even though basal uptake was elevated due to prolonged preincubation with insulin. The cells were insulin-resistant.

When E-64 was included with insulin during the preincubation period, insulin resistance was ameliorated. Pretreatment with E-64 and insulin resulted in cells which were more sensitive to insulin action, with 10 nM insulin inducing a five fold stimulation of lipogenesis as compared with the three-fold stimulation seen in control cells.

Example 3

Treatment of Genetically Obese, Insulin Resistant Rats with E-64

Genetically obese, Zucker fatty rats were injected intraperitoneally (I.P.) with control vehicle (normal saline) or E-64 (2.5 mg/kg) every 24 hours ±2 hours. The injection protocol was initiated when the rats were 14 weeks old, a time when their insulin resistant state was fully manifest. Blood was drawn from the animals at intervals before the beginning of the injection schedule, and at at least one week intervals after initiating the injections. On the first day of the protocol, the fatty rats weighed an average of 416 grams. On the final day of the protocol (day 90), the animals weighed an average of 550 grams.

This same protocol was also performed using lean Zucker rats. At the beginning of the protocol, the average weight of the lean animals was 225 grams. At the conclusion of the protocol, the average weight of the lean animals was 260 grams. Also at the beginning of the protocol, the average serum triglycerides level of the lean rats was 60 mg/dl, and at the end of the protocol, the average triglyceride level of the lean rats was 120 mg/dl. E-64 had no effect on the triglyceride levels in the lean rats (data not shown). In contrast, and as shown in Table 3, injection of E-64 prevented the increase in triglyceride levels found in the control Zucker fatty rats.

TABLE 3

| TREATMENT | DAY OF PROTOCOL | SERUM TG MG/DL (n = 3) |
|---|---|---|
| Fatty, control | −4 | 947 ± 301 |
| Fatty, E-64 |  | 1009 ± 157 |
| Fatty, control | 28 | 1376 ± 278 |
| Fatty, E-64 |  | 798 ± 269 |
| Fatty, control | 56 | 1401 ± 311 |
| Fatty, E-64 |  | 1045 ± 443 |
| Fatty, control | 89 | 1659 ± 277 |
| Fatty, E-64 |  | 1093 ± 301 |

E-64 at the concentrations and injection schedules described reduced but did not reverse the insulin resistant state in Zucker fatty rats. It is expected that the protocol may be optimized, e.g., by increasing the daily dose of E-64, or initiating the protocol prior to the onset of insulin resistance. Additional optimization studies will reveal doses and schedules of thiol protease treatment which result in decreased serum triglyceride levels, and therefore in a reversal of the insulin-resistant state.

Example 4

Inhibition of Insulin-Induced Receptor Autophosphorylation by the Insulin Receptor Fragment β'

Insulin receptor (50 fmol insulin binding activity per assay) and varying amounts of partially purified β' insulin receptor fragment were incubated in the presence or absence of insulin (100 nM) for 30 minutes and at room temperature. $^{32}$P-ATP was then added to the reaction mixture to a final concentration of 50 µM, and the reaction was allowed to proceed for an additional 30 minutes. The reaction was then terminated by the addition of SDS-PAGE sample buffer, boiled, and the components of the mixture resolved by SDS polyacrylamide gel electrophoresis. The electrophoresed gel was exposed to x-ray film to visualize the band corresponding to the intact β subunit of the insulin receptor. This band was excised from the gel and the amount of radioactivity contained in the band was quantitated by Cherenkov counting in a scintillation counter. The results are shown in Table 4.

TABLE 4

| B' (µl) | CPM (Insulin) − | CPM (Insulin) + | FOLD STIMULATION |
|---|---|---|---|
| 0 | 190 | 590 | 3.1 |
| 10 | 180 | 450 | 2.5 |
| 20 | 200 | 420 | 2.1 |
| 30 | 200 | 320 | 1.6 |

As shown in Table 4, the β' fragment had no effect on basal phosphorylation of the insulin receptor (in the absence of insulin). In contrast, as the concentration of β' was increased, insulin-induced autophosphorylation of the insulin receptor was decreased. Thus, the β' insulin receptor fragment inhibited insulin receptor autophosphorylation, and thereby inhibited the first step in the insulin signal transduction pathway. These data suggest that the presence of β' in an intact cell leads to insulin resistance.

I claim:

1. A method for treating Type II diabetes mellitus comprising administering to a subject suffering from Type II diabetes a therapeutically effective dose of a thiol protease inhibitor which inhibits the production of the β' fragment of the insulin receptor.

2. A method for treating Type II diabetes mellitus comprising administering to a subject suffering from Type II diabetes the thiol protease inhibitor L-transepoxysuccinyl-leucylamido (4-guanidino) butane.

3. A method for treating insulin resistance comprising administering to a subject suffering from insulin resistance a therapeutically effective dose of a thiol protease inhibitor which inhibits the production of the β' fragment of the insulin receptor.

4. A method for treating insulin resistance comprising administering to a subject in need thereof a therapeutically effective dose of a thiol protease inhibitor, wherein the thiol protease inhibitor is L-transepoxysuccinyl-leucylamido (4-guanidino) butane.

5. A method for treating insulin resistance comprising administering to a subject a therapeutically effective dose of the thiol protease inhibitor, leupeptin.

* * * * *